United States Patent [19]
Buzzetti et al.

[11] Patent Number: 5,840,745
[45] Date of Patent: Nov. 24, 1998

[54] HYDROSOLUBLE 3-ARYLIDENE-2-OXINDOLE DERIVATIVES AS TYROSINE KINASE INHIBITORS

[75] Inventors: Franco Buzzetti, Monza; Maria Gabriella Brasca, Cusago; Antonio Longo, Milan; Dario Ballinari, San Donato Milanese, all of Italy

[73] Assignee: Pharmacia S. p. A., Milan, Italy

[21] Appl. No.: 704,760

[22] PCT Filed: Dec. 22, 1995

[86] PCT No.: PCT/EP95/05176

§ 371 Date: Sep. 25, 1996

§ 102(e) Date: Sep. 25, 1996

[87] PCT Pub. No.: WO96/22976

PCT Pub. Date: Aug. 1, 1996

[30] Foreign Application Priority Data

Jan. 26, 1995 [GB] United Kingdom ................ 9501567.3

[51] Int. Cl.$^6$ ........................ A61K 31/40; C07D 209/14; C07D 209/34; C07D 211/06
[52] U.S. Cl. ......................... 514/414; 514/415; 514/418; 544/98; 544/128; 544/144; 544/175; 544/337; 544/358; 544/363; 544/364; 544/373; 546/184; 546/201; 546/208; 548/454; 548/455; 548/469; 548/486; 548/488
[58] Field of Search .................................... 514/414, 415, 514/418; 544/98, 128, 144, 175, 337, 358, 363, 364, 373; 546/184, 201, 208; 548/454, 455, 469, 486, 488

[56] References Cited

U.S. PATENT DOCUMENTS

| | | | |
|---|---|---|---|
| 4,486,442 | 12/1984 | Friebe et al. ............................ | 424/267 |
| 5,300,655 | 4/1994 | Ehrgott et al. ........................... | 549/71 |
| 5,374,652 | 12/1994 | Buzzetti et al. .......................... | 514/418 |

FOREIGN PATENT DOCUMENTS 9501349  1/1995  Italy .

OTHER PUBLICATIONS

*Organic Preparations* by Conrad Weygard; pp. 422–426; Interscience Publishers, Ltd., New York, N.Y. (1945).

"Inhibitors of Protein Kinase C. 2. Substituted Bisindolylmaleimides with Improved Potency and Selectivity," Peter D. Davis et al., *J. Med. Chem.* 1992, 35, 994–1001.

*Organic Reactions*, G. Jones, 15, 204 (1967).

*Methoden der Organischen Chemie*, Houben–Weyl, vol. XI/I, p. 311 (1957); vol. E5, p. 960 (1985); vol. IX, p. 609 (1955); vol E4, p. 362 (1983); vol. VI/3, p. 54 (1965);

*Methoden der Organischen Chemie*, Houben–Weyl, vol. VIII, p. 543 (1952); vol. XII/2, p. 143 (1964); vol. III, p. 508 (1952); vol. VIII, pp. 697 and 702 (1952); vol. XI/I, p. 24, (1957).

*Organic Reactions*, S.J. Augyal, 8, p. 197 (1959).

*Primary Examiner*—Johann Richter
*Assistant Examiner*—Jane C. Oswecki
*Attorney, Agent, or Firm*—Oblon, Spivak, McClelland, Maier & Neustadt, P.C.

[57] ABSTRACT

Novel hydrosoluble 3-arylidene-2-oxindole derivatives, having tyrosine kinase inhibitor activity, encompassed by general formula (I), wherein m is zero, 1 or 2; A is a bicyclic ring chosen from tetralin, naphthalene, quinoline and indole; $R^1$ is hydrogen, $C_1$–$C_6$ alkyl or $C_2$–$C_6$ alkanoyl; one of $R^2$ and $R^3$ independently is hydrogen and the other is a substituent selected from: a $C_1$–$C_6$ alkyl group substituted by 1, 2 or 3 hydroxy groups; —$SO_3R^4$ in which $R^4$ is hydrogen or $C_1$–$C_6$ alkyl unsubstituted or substituted by 1, 2 or 3 hydroxy groups; —$SO_2NHR^5$ in which $R^5$ is as $R^4$ defined above or a —$(CH_2)_n$—$N(C_1$–$C_6$ alkyl$)_2$ group in which n is 2 or 3; —$COOR^6$ in which $R^6$ is $C_1$–$C_6$ alkyl unsubstituted or substituted by phenyl or by 1, 2 or 3 hydroxy groups or phenyl; —$CONHR^7$ in which $R^7$ is hydrogen, phenyl or $C_1$–$C_6$ alkyl substituted by 1, 2 or 3 hydroxy groups or by phenyl; —$NHSO_2R^8$ in which $R^8$ is $C_1$–$C_6$ alkyl or phenyl unsubstituted or substituted by halogen or by $C_1$–$C_4$ alkyl; —$N(R^9)_2$, —$NHR^9$ or —$OR^9$ wherein $R^9$ is $C_2$–$C_6$ alkyl substituted by 1, 2 or 3 hydroxy groups; —$NHCOR^{10}$, —$OOCR^{10}$ or —$CH_2OOCR^{10}$ in which $R^{10}$ is $C_1$–$C_6$ alkyl substituted by 1, 2 or 3 hydroxy groups; —$NHCONH_2$; —$NH$—$C(NH_2)$=$NH$; —$C(NH_2)$=$NH$; —$CH_2NHC(NH_2)$=$NH$; —$CH_2NH_2$; —$OPO(OH)_2$; —$CH_2OPO(OH)_2$; —$PO(OH)_2$; or (a), (b), (c), or (d) group, wherein p is 1, 2 or 3 and Z is —$CH_2$—, —O— or (e), in which $R^{11}$ is hydrogen or is as $R^9$ defined above; and the pharmaceutically acceptable salts thereof, are disclosed.

13 Claims, No Drawings

HYDROSOLUBLE 3-ARYLIDENE-2-OXINDOLE DERIVATIVES AS TYROSINE KINASE INHIBITORS

This application is a 371 of PCT/EP95/05176 of Dec. 22, 1995.

The present invention relates to new hydrosoluble 3-arylidene-2-oxindole derivatives, to a process for their preparation, to pharmaceutical compositions containing them and to their use as therapeutic agents, in particular as tyrosine kinase inhibitors. The present invention provides novel hydrosoluble 3-arylidene-2-oxindole derivatives having the following general formula (I)

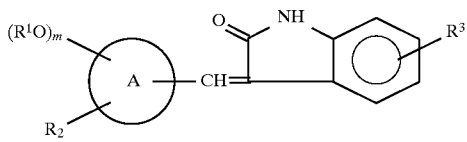

wherein
m is zero, 1 or 2;
A is a bicyclic ring chosen from tetralin, naphthalene, quinoline and indole;
$R^1$ is hydrogen, $C_1$–$C_6$ alkyl or $C_2$–$C_6$ alkanoyl;
one of $R^2$ and $R^3$ independently is hydrogen and the other is a substituent selected from:
a $C_1$–$C_6$ alkyl group substituted by 1, 2 or 3 hydroxy groups;
—$SO_3R^4$ in which $R^4$ is hydrogen or $C_1$–$C_6$ alkyl unsubstituted or substituted by 1, 2 or 3 hydroxy groups;
—$SO_2NHR^5$ in which $R^5$ is as $R^4$ defined above or a —$(CH_2)_n$—$N(C_1$–$C_6$ alkyl$)_2$ group in which n is 2 or 3;
—$COOR^6$ in which $R^6$ is $C_1$–$C_6$ alkyl unsubstituted or substituted by phenyl or by 1, 2 or 3 hydroxy groups or phenyl;
—$CONHR^7$ in which $R^7$ is hydrogen, phenyl or $C_1$–$C_6$ alkyl substituted by 1, 2 or 3 hydroxy groups or by phenyl;
—$NHSO_2R^8$ in which $R^8$ is $C_1$–$C_6$ alkyl or phenyl unsubstituted or substituted by halogen or by $C_1$–$C_4$ alkyl;
—$N(R^9)_2$, —$NHR^9$ or —$OR^9$ wherein $R^9$ is $C_2$–$C_6$ alkyl substituted by 1, 2 or 3 hydroxy groups;
—$NHCOR^{10}$, —$OOCR^{10}$ or —$CH_2OOCR^{10}$ in which $R^{10}$ is $C_1$–$C_6$ alkyl substituted by 1, 2 or 3 hydroxy groups;
—$NHCONH_2$; —NH—C($NH_2$)=NH; —C($NH_2$)=NH; —$CH_2NHC(NH_2)$=NH;
—$CH_2NH_2$; —$OPO(OH)_2$; —$CH_2OPO(OH)_2$; —$PO(OH)_2$; or a

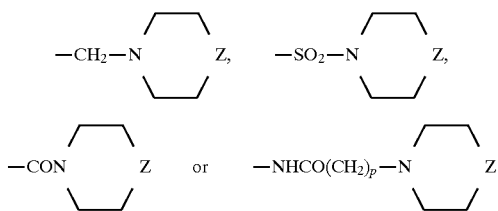

group,
wherein p is 1, 2 or 3 and Z is —$CH_2$—, —O— or >N—$R^{11}$ in which $R^{11}$ is hydrogen or is as $R^9$ defined above; and the pharmaceutically acceptable salts thereof.

The substituents $R^1O$ and $R^2$ may be independently on either of the ring moieties whereas the $R^3$ substituent is only linked to the benzene moiety.

The invention includes within its scope all the possible isomers, stereoisomers, in particular Z- and E-isomers and their mixtures, and the metabolites and the metabolic precursors or bio-precursors (otherwise known as pro-drugs) of the compound of formula (I).

The oxindolylidene substituent is preferably linked to position 1 or 2 when A is tetralin or naphthalene, to position 4 or 5 when A is quinoline and to position 3 when A is indole.

The $R^3$ substituent is preferably linked to position 5 in the oxindole ring.

The $R^2$ substituent with reference to the oxindolylidene substituent is preferably linked to the same ring moiety when A is tetralin, whereas it is preferably linked to the other ring moiety when Ar is naphthalene, quinoline or indole.

The $OR^1$ substituent is preferably located on the same benzene moiety when A is tetralin, quinoline or indole whereas it may be located on either benzene moieties when A is naphthalene.

m is preferably zero when $R^2$ is not hydrogen.

Of course only one of the substituents $R^1O$ and $R^2$ can be linked to the same ring position.

An alkyl group or an alkyl moiety in an alkanoyl group may be branched or straight alkyl chain.

A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl.

A $C_2$–$C_6$ alkyl group is preferably a $C_2$–$C_4$ alkyl group in particular ethyl.

A $C_1$–$C_6$ alkyl group substituted by 1 to 3 hydroxy groups is, for instance, a $C_1$–$C_4$ alkyl group substituted by 1 or 2 hydroxy groups, typically a —$CH_2OH$, —$CHOHCH_2OH$ or —$CH_2(CHOH)_qCH_2OH$ group in which q is zero or 1.

A halogen atom is for example chloro, bromo or iodo, in particular chloro.

A $C_1$–$C_6$ alkyl group substituted by phenyl is typically benzyl or phenylethyl.

A $C_2$–$C_6$ alkanoyl group is preferably a $C_2$–$C_3$ alkanoyl group, in particular acetyl or propionyl.

The term tetralin is meant to refer to 5,6,7,8-tetrahydronaphthalene.

Pharmaceutically acceptable salts of the compounds of the invention include acid addition salts with inorganic, e.g. nitric, hydrochloric, hydrobromic, sulphuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium bases or alkaline-earth metal, especially calcium or magnesium bases, or with organic bases, e.g. acyclic or cyclic amines, preferably triethylamine or piperidine.

As stated above, the present invention also includes within its scope pharmaceutically acceptable bio-precursors (otherwise known as pro-drugs) of the compounds of formula (I), i.e. compounds which have a different formula to formula (I) above but which, nevertheless, upon administration to a human being are converted directly or indirectly in vivo into a compound of formula (I).

Preferred compounds of the invention are the compounds of formula (I) wherein
A and m are as defined above;
$R^1$ is hydrogen or $C_1$–$C_4$ alkyl;
one of $R^2$ and $R^3$ independently is hydrogen and the other is a substituent selected from —$SO_3H$; —$SO_2NH_2$; $COOR^6$ wherein $R^6$ is $C_1$–$C_4$ alkyl or benzyl, —CONHR$^7$ wherein $R^7$ is phenyl or benzyl; —N(CH$_2$CH$_2$OH)$_2$; —NHCH$_2$CHOHCH$_2$OH; —NHCONH$_2$; —NHC(NH$_2$)=NH; —NHCOCHOHCH$_2$OH;

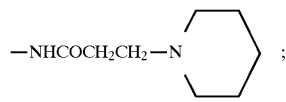

—NHSO$_2$C$_1$–C$_4$ alkyl; —OCH$_2$CHOHCH$_2$OH; —OOCCH$_2$OH; —CH$_2$NH$_2$; —OH$_2$OH; —C(NH$_2$)=NH and —OPO(OH)$_2$; and the pharmaceutically acceptable salts thereof.

Examples of specific compounds of the invention are the following compounds, which, when appropriate, may be either Z- or E-diastereomers or Z,E-mixtures of said diastereomers:

5-sulfo-3-[1,4-dihydroxytetral-2-ylmethylene]-2-oxindole;
5-sulfamoyl-3-[1,4-dihydroxytetral-2-ylmethylene]-2-oxindole;
5-sulfo-3-[1-hydroxytetral-2-ylmethylene]-2-oxindole;
5-sulfamoyl-3-[1-hydroxytetral-2-ylmethylene]-2-oxindole;
5-sulfo-3-[3-hydroxytetral-2-ylmethylene]-2-oxindole;
5-sulfamoyl-3-[3-hydroxytetral-2-ylmethylene]-2-oxindole;
5-sulfo-3-[4-hydroxytetral-1-ylmethylene]-2-oxindole;
5-sulfamoyl-3-[4-hydroxytetral-1-ylmethylene]-2-oxindole;
5-carbomethoxy-3-[1,4-dihydroxytetral-2-ylmethylene]-2-oxindole;
5-carbomethoxy-3-[3-hydroxytetral-2-ylmethylene]-2-oxindole;
5-diethanolamino-3-(1,4-dihydroxytetral-2-ylmethylene)-2-oxindole;
5-(2,3-dihydroxypropylamino)-3-(1,4-dihydroxytetral-2-ylmethylene)-2-oxindole;
5-ureido-3-(1,4-dihydroxytetral-2-ylmethylene)-2-oxindole;
5-guanidino-3-(1,4-dihydroxytetral-2-ylmethylene)-2-oxindole;
5-glyceroylamido-3-(1,4-dihydroxytetral-2-ylmethylene)-2-oxindole;
5-(3-piperidinopropionylamino)-3-(1,4-dihydroxytetral-2-ylmethylene)-2-oxindole;
5-mesylamino-3-(1,4-dihydroxytetral-2-ylmethylene)-2-oxindole;
5-glycoloyloxy-3-(1,4-dihydroxytetral-2-ylmethylene)-2-oxindole;
5-(2,3-dihydroxypropoxy)-3-(1,4-dihydroxytetral-2-ylmethylene)-2-oxindole;
5-aminomethyl-3-(1,4-dihydroxytetral-2-ylmethylene)-2-oxindole;
5-amidino-3-(1,4-dihydroxytetral-2-ylmethylene)-2-oxindole;
5-hydroxymethyl-3-(1,4-dihydroxytetral-2-ylmethylene)-2-oxindole;
5-phosphonooxy-3-(1,4-dihydroxytetral-2-ylmethylene)-2-oxindole;
5-sulfo-3-(quinol-4-ylmethylene)-2-oxindole;
5-sulfamoyl-3-(quinol-4-ylmethylene)-2-oxindole;
5-carbomethoxy-3-(quinol-4-ylmethylene)-2-oxindole;
5-diethanolamino-3-(quinol-4-ylmethylene)-2-oxindole;
5-(2,3-dihydroxypropylamino)-3-(quinol-4-ylmethylene)-2-oxindole;
5-ureido-3-(quinol-4-ylmethylene)-2-oxindole;
5-guanidino-3-(quinol-4-ylmethylene)-2-oxindole;
5-glyceroylamido-3-(quinol-4-ylmethylene)-2-oxindole;
5-(3-piperidinopropionylamino)-3-(quinol-4-ylmethylene)-2-oxindole;
5-mesylamino-3-(quinol-4-ylmethylene)-2-oxindole;
5-glycoloyloxy-3-(quinol-4-ylmethylene)-2-oxindole;
5-(2,3-dihydroxypropoxy)-3-(quinol-4-ylmethylene)-2-oxindole;
5-aminomethyl-3-(quinol-4-ylmethylene)-2-oxindole;
5-amidino-3-(quinol-4-ylmethylene)-2-oxindole;
5-hydroxymethyl-3-(quinol-4-ylmethylene)-2-oxindole;
5-phosphonooxy-3-(quinol-4-ylmethylene)-2-oxindole;
5-sulfo-3-(indol-3-ylmethylene)-2-oxindole;
5-sulfamoyl-3-(indol-3-ylmethylene)-2-oxindole;
5-carbomethoxy-3-(indol-3-ylmethylene)-2-oxindole;
5-diethanolamino-3-(indol-3-ylmethylene)-2-oxindole;
5-(2,3-dihydroxypropylamino)-3-(indol-3-ylmethylene)-2-oxindole;
5-ureido-3-(indol-3-ylmethylene)-2-oxindole;
5-guanidino-3-(indol-3-ylmethylene)-2-oxindole;
5-glyceroylamido-3-(indol-3-ylmethylene)-2-oxindole;
5-(3-piperidinopropionylamino)-3-(indol-3-ylmethylene)-2-oxindole;
5-mesylamino-3-(indol-3-ylmethylene)-2-oxindole;
5-glycoloyloxy-3-(indol-3-ylmethylene)-2-oxindole;
5-(2,3-dihydroxypropoxy)-3-(indol-3-ylmethylene)-2-oxindole;
5-aminomethyl-3-(indol-3-ylmethylene)-2-oxindole;
5-amidino-3-(indol-3-ylmethylene)-2-oxindole;
5-hydroxymethyl-3-(indol-3-ylmethylene)-2-oxindole;
5-phosphonooxy-3-(indol-3-ylmethylene)-2-oxindole;
3-(5-sulfoindol-3-ylmethylene)-2-oxindole;
3-(5-sulfamoylindol-3-ylmethylene)-2-oxindole;
3-(5-carbomethoxyindol-3-ylmethylene)-2-oxindole;
3-(5-diethanolamino-3-indolylmethylene)-2-oxindole;
3-[5-(2,3-dihydroxypropylamino)-3-indolylmethylene]-2-oxindole;
3-(5-ureido-3-indolylmethylene)-2-oxindole;
3-(5-guanidino-3-indolylmethylene)-2-oxindole;
3-(5-glyceroylamido-3-indolylmethylene)-2-oxindole;
3-[5-(3-piperidinopropionylamino)-3-indolylmethylene]-2-oxindole;
3-(5-mesylamino-3-indolylmethylene)-2-oxindole;
3-(5-glycoloyloxy-3-indolylmethylene)-2-oxindole;
3-[5-(2,3-dihydroxypropoxy)-3-indolylmethylene]-2-oxindole;
3-(5-aminomethyl-3-indolylmethylene)-2-oxindole;
3-(5-amidino-3-indolylmethylene)-2-oxindole;
3-(5-hydroxymethyl-3-indolylmethylene)-2-oxindole;
3-(5-phosphonooxy-3-indolylmethylene)-2-oxindole;
5-sulfo-3-(naphth-2-ylmethylene)-2-oxindole;
5-sulfamoyl-3-(naphth-2-ylmethylene)-2-oxindole;
5-carbomethoxy-3-(naphth-2-ylmethylene)-2-oxindole;
5-diethanolamino-3-(naphth-2-ylmethylene)-2-oxindole;
5-(2,3-dihydroxypropylamino)-3-(naphth-2-ylmethylene)-2-oxindole;
5-ureido-3-(naphth-2-ylmethylene)-2-oxindole;
5-guanidino-3-(naphth-2-ylmethylene)-2-oxindole;
5-glyceroylamido-3-(naphth-2-ylmethylene)-2-oxindole;
5-(3-piperidinopropionylamino)-3-(naphth-2-ylmethylene)-2-oxindole;
5-mesylamino-3-(naphth-2-ylmethylene)-2-oxindole;
5-glycoloyloxy-3-(naphth-2-ylmethylene)-2-oxindole;
5-(2,3-dihydroxypropoxy)-3-(naphth-2-ylmethylene)-2-oxindole;
5-aminomethyl-3-(naphth-2-ylmethylene)-2-oxindole;
5-amidino-3-(naphth-2-ylmethylene)-2-oxindole;
5-hydroxymethyl-3-(naphth-2-ylmethylene)-2-oxindole;
5-phosphonooxy-3-(naphth-2-ylmethylene)-2-oxindole;
5-sulfo-3-(1-hydroxytetral-2-ylmethylene)-2-oxindole;
5-sulfo-3-(4-hydroxytetral-2-ylmethylene)-2-oxindole;
5-(3-piperidinopropionylamino)-3-(5-methoxyindol-3-ylmethylene)-2-oxindole;

3-[5-(p-chlorophenyl)sulfonylamidoindol-3-yl-methylene]-2-oxindole;
5-carboethoxy-3-(3-hydroxytetral-2-ylmethylene)-2-oxindole;
5-carboethoxy-3-(quinol-4-ylmethylene)-2-oxindole;
5-carboethoxy-3-(5-methoxyindol-3-ylmethylene)-2-oxindole;
3-(5-carboethoxyindol-3-ylmethylene)-2-oxindole;
5-carbobenzyloxy-3-(3-hydroxytetral-2-ylmethylene)-2-oxindole;
5-carbobenzyloxy-3-(quinol-4-ylmethylene)-2-oxindole;
5-carbobenzyloxy-3-(5-methoxyindol-3-ylmethylene)-2-oxindole;
3-(5-carbobenzyloxyindol-3-ylmethylene)-2-oxindole;
5-phenylcarbamoyl-3-(3-hydroxytetral-2-ylmethylene)-2-oxindole;
5-phenylcarbamoyl-3-(quinol-4-ylmethylene)-2-oxindole;
5-phenylcarbamoyl-3-(5-methoxyindol-3-ylmethylene)-2-oxindole;
3-(5-phenylcarbamoylindol-3-ylmethylene)-2-oxindole;
5-benzylcarbamoyl-3-(3-hydroxytetral-2-ylmethylene)-2-oxindole;
5-benzylcarbamoyl-3-(quinol-4-ylmethylene)-2-oxindole;
5-benzylcarbamoyl-3-(5-methoxyindol-3-ylmethylene)-2-oxindole;
3-(5-benzylcarbamoylindol-3-ylmethylene)-2-oxindole;
5-carboethoxy-3-(8-hydroxyquinol-5-ylmethylene)-2-oxindole;
5-benzylcarbamoyl-3-(8-hydroxyquinol-5-ylmethylene)-2-oxindole;
5-(2,3-dihydroxypropylamino)-3-(5-methoxy-3-indolylmethylene)-2-oxindole;
5-sulfo-3-(5-methoxyindol-3-ylmethylene)-2-oxindole;
5-amidino-3-(5-methoxyindol-3-ylmethylene)-2-oxindole, and the pharmaceutically acceptable salts thereof.

The compounds of the invention, and the salts thereof, can be obtained by a process comprising:

a) condensation of an aldehyde of formula (II)

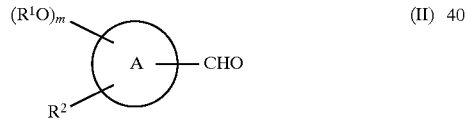

wherein A, $R^1$, $R^2$ and m are as defined above, with a compound of formula (III)

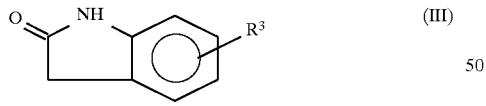

wherein $R^3$ is as defined above; or b) N-alkylation of a compound of formula (IV)

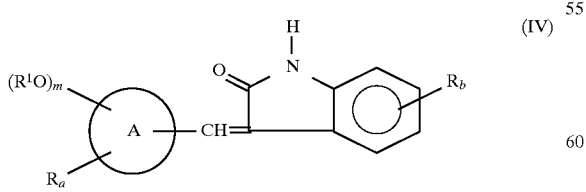

wherein $R^1$, A and m are as defined above, and one of $R_a$ and $R_b$ is —$NH_2$ and the other is hydrogen, thus obtaining a compound of formula (I) wherein one of $R^2$ and $R^3$ is a group —$NHR^9$ or —$N(R^9)_2$ in which $R^9$ is as defined above and the other is hydrogen; or c) N-acylating a compound of formula (IV), as defined above, thus obtaining a compound of formula (I) wherein one of $R^2$ and $R^3$ is a —$NHCOR^{10}$ or

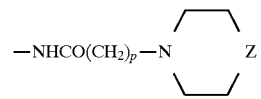

group, in which $R^{10}$, p and Z are as defined above and the other is hydrogen; or d) N-sulfonylation of a compound of formula (IV), as defined above, thus obtaining a compound of formula (I), wherein one of $R^2$ and $R^3$ is hydrogen and the other is —$NHSO_2R^8$ in which $R^8$ is as defined above; or e) N-amidination of a compound of formula (IV), as defined above, thus obtaining a compound of formula (I), wherein one of $R^2$ and $R^3$ is hydrogen and the other is —$NHC(NH_2)=NH$; or f) N-carbamoylation of a compound of formula (IV), as defined above, thus obtaining a compound of formula (I), wherein one of $R^2$ and $R^3$ is hydrogen and the other is —$NHCONH_2$; or g) O-alkylation of a compound of formula (V)

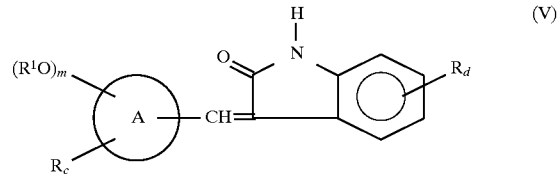

wherein $R^1$, m and A are as defined above, one of $R_c$ and $R_d$ is —OH and the other is hydrogen, thus obtaining a compound of formula (I) wherein one of $R^2$ and $R^3$ is a group —$OR^9$ in which $R^9$ is as defined above and the other is hydrogen; or h) O-acylating of a compound of formula (V), as defined above, thus obtaining a compound of formula (I) wherein one of $R^2$ and $R^3$ is hydrogen and the other is a group —$OOCR^{10}$ in which $R^{10}$ is as defined above; or i) O-phosphorylation of a compound of formula (V), as defined above, thus obtaining a compound of formula (I), wherein one of $R^2$ and $R^3$ is hydrogen and the other is —$OPO(OH)_2$; or k) esterification of a compound of formula (VI)

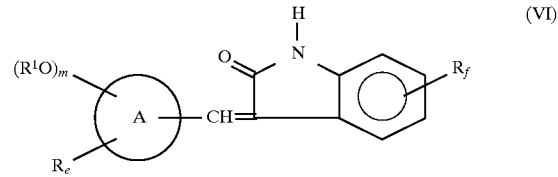

wherein $R^1$, m and A are as defined above and one of $R_e$ and $R_f$ is —COOH and the other is hydrogen, thus obtaining a compound of formula (I), wherein one of $R^2$ and $R^3$ is hydrogen and the other is —$COOR^6$ in which $R^6$ is as defined above; or l) ammonia addition to a compound of formula (VII)

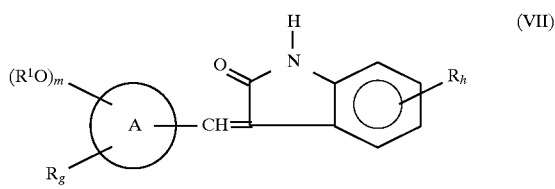

wherein $R^1$, A and m are as defined above and one of $R_g$ and $R_h$ is —CN and the other is hydrogen, thus obtaining a compound of formula (I), wherein one of $R^2$ and $R^3$ is hydrogen and the other is —C($NH_2$)=NH; or m) amination of a compound of formula (VIII)

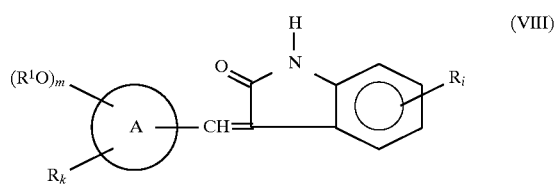

wherein $R^1$, m and A are as defined above and one of $R_k$ and $R_i$ is —$CH_2Cl$ and the other is hydrogen, thus obtaining a compound of formula (I), wherein one of $R^2$ and $R^3$ is hydrogen and the other is a —$CH_2NH_2$ or

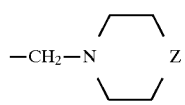

group in which Z is as defined above; and, if desired, the conversion of a compound of formula (I) into another compound of formula (I), and/or, if desired, the conversion of a compound of formula (I) into a salt thereof, and/or, if desired, converting a salt of a compound of formula (I) into a free compound of formula (I), and/or, if desired, separating a mixture of isomers of a compound of formula (I) into the single isomers.

The condensation of a compound of formula (II) with a compound of formula (III) according to process step a) may be carried out using known methods, e.g. under the conditions of the Knoevenagel reaction as described, e.g., by G. Jones in organic Reactions 15, 204 (1967). Suitable reaction catalysts are organic bases such as pyridine, piperidine, diethylamine or triethylamine.

The condensation may be performed in an inert organic solvent, e.g. pyridine, a lower alkanol, e.g. ethanol, methanol, benzene or dioxane at temperatures ranging from about 0° to about 100° C. Preferably the reaction is carried out in warm ethanol solution in the presence of piperidine catalyst.

The N-alkylation according to process step b) may be carried out according to known methods, e.g. as described in Houben-Weyl, Methoden der Organischen Chemie, Vol. XI/I, page 311 (1957). In particular, in order to obtain compounds of formula (I) wherein $R^2$ or $R^3$ is —N($CH_2CH_2OH)_2$, the aromatic amine of formula (IV) is reacted with ethylene oxide in water, alcoholic or hydroalcoholic solution at temperatures ranging, e.g., from 0° to 100° C. Preferably the reaction is carried out in hydroalcoholic suspension at about 70°–80° C. by introducing ethylene oxide gas. N-alkylation according to process step b) in order to obtain compounds of formula (I) wherein $R^2$ or $R^3$ is, for instance, —$NHCH_2$—CHOH—$CH_2OH$ can be carried out by reductive amination, i.e. by condensation of the aromatic amine of formula (IV) with an aldehyde of formula $CH_2OHCHOHCHO$ in the presence of a reducing agent, e.g. as described in Tietze and Eiche, Reactions and Synthesis in the organic Chemistry Laboratory, page 77 (1988). Thus to the alcoholic solution of the aromatic amine and the aldehyde is added portionwise sodium cyanoborohydride at temperatures ranging from 0° C. to reflux temperature.

The N-acylation according to process step c) may be carried out by known methods, e.g. as described in Houben-Weyl, Methoden der Organischen Chemie, vol. E5, page 960 (1985). Thus the aromatic amine is reacted with the corresponding carboxylic acid of formula $R^{10}$—COOH or

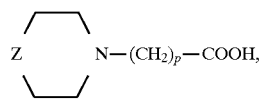

wherein $R^{10}$, Z and p are as defined above, by using a condensing agent such as dicyclohexylcarbodiimide (DCCD). Preferably equimolar amounts of amine, acid and DCCD are used in an inert solvent such as THF or benzene at temperatures from about 0° C. to 50° C.

The N-sulfonylation according to process step d) may be carried out by known methods, e.g. as described in Houben-Weyl, Vol. IX, page 609 (1955). Thus equimolar amounts of aromatic amine and sulfochloride of general formula $R^8$—$SO_2Cl$ are reacted in pyridine solution at temperatures from about –10° C. to 50° C.

The N-amidination according to process step e) may be carried out, e.g., as described by P. D. Davis et al. in J. Med. Chem. 1992, 35, 994. Thus the aromatic amine is treated with about 1.5 molequivalents of 3,5-dimethyl-pyrazole-1-carboxamidine in refluxing ethanol in the presence of about 1 molequivalent of $NaHCO_3$.

The N-carbamoylation according to process step f) may be carried out, e.g., as described in Houben-Weyl, Vol. E4, page 362 (1983). Thus the aromatic amine salt, preferably the hydrochloride salt, is reacted with an alkali metal cyanate, preferably NaOCN or KOCN, in aqueous or hydroalcoholic solution at temperatures ranging from about 50° C. to about 100° C.

The O-alkylation according to process step g) may be performed, e.g., as described in Houben-Weyl, Vol. VI/3, page 54 (1965). Thus the phenol is first transformed into its alkali metal salt by treatment with an alkali metal alcoholate or hydroxide or amide. Then the phenolate is reacted with a halogenide of general formula $R^9$—X, in which $R^9$ is as defined above and X is chlorine or bromine, in an inert solvent such as benzene or THF at temperatures ranging from room to reflux temperatures. Preferably the reaction is performed in benzene solution by reacting the phenol first with a stoichiometric amount of $NaNH_2$ at room temperature and then with an excess of halogenide at reflux temperature.

The O-acylation according to process step h) may be carried out by known methods, e.g. as reported in Houben-Weyl, Vol. VIII, page 543 (1952). Thus the phenol is reacted with the acid halide of general formula $R^{10}$—COCl, wherein $R^{10}$ is as defined above, in the presence of an organic base such as pyridine or triethylamine at temperatures ranging from about 0° to 50° C. in an appropriate organic solvent. Alternatively the phenol is reacted with the acid $R^{10}$—COOH, in which $R^{10}$ is as defined above, in the presence of a condensing agent such as dicyclohexylcarbodiimide (DCCD). Preferably equimolar amounts of phenol and DCCD are used and the reaction is performed in an inert solvent such as THF or benzene at temperatures from about 0° to 50° C.

The O-phosphorylation according to process step i) can be carried out by known methods, e.g. as described in Houben-Weyl, Vol. XII/2, page 143 (1964). Thus the phenol is reacted with phosphoric acid or a derivative thereof in water or hydroalcoholic solution at temperatures ranging from room to reflux temperatures. Preferably the reaction is performed in polyphosphoric acid (mixture of $H_3PO_4$ and $P_2O_5$) which acts as reactant and solvent at temperatures ranging from about $50°$ to $100°$ C.

The esterification according to process step k) can be carried out by well known methods, e.g. as reported in Houben-Weyl, Vol. VIII, page 508 (1952). Thus the mixture of acid and alcohol, dissolved in an inert solvent such as benzene and chloroform, is heated to reflux in the presence of a mineral acid such as $H_2SO_4$ or HCl. Preferably the water formed is removed by azeotropic distillation in a Dean-Stark condenser.

The nitrile transformation according to process step l) can be carried out by known methods, as described in Houben-Weyl, Vol. VIII, pages 697 and 702 (1952). Thus to the ether or chloroform solution of the nitrile is added an equimolar amount of ethanol and the solution is saturated with HCl gas. The resulting iminoether hydrochloride is then transformed into the amidine by reaction with ammonia in absolute ethanol at room temperature.

The amination according to process step m) can be performed by known methods, e.g. as reported in Houben-Weyl, Vol.XI/I, page 24 (1957). Thus a mixture of chloromethyl compound and secondary amino derivative is treated at temperatures from about 50° to about 150° C. until the reaction is complete. Otherwise, the amination of the chloromethyl compound in order to obtain an aminomethyl compound can be performed according to the Delepine reaction as described by S. J. Augyal in Organic Reactions 8, 197 (1959). Thus the benzylhalide is first reacted with hexamethylenetetramine to give a quaternary ammonium salt which is then cleaved by acid hydrolysis.

The optional salification of a compound of formula (I) as well as the conversion of the salt into the corresponding free compound and the separation of a mixture of isomers into the single isomers as well as the conversion of a compound of formula (I) into another compound of formula (I) may be carried out according to known methods. For example, the amidation of a compound of formula (I), wherein $R^2$ or $R^3$ is —$SO_3H$, so as to obtain a compound of formula (I) wherein $R^2$ or $R^3$ is —$SO_2NHR^5$ or

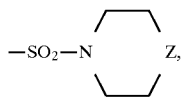

in which $R^5$ and Z are as defined above, may be carried out by known methods, e.g. as described at process step d). The conversion of a compound of formula (I) in which $R^2$ or $R^3$ is —$CH_2NH_2$ into a compound of formula (I) wherein $R^2$ or $R^3$ is —$CH_2NH$—$C(NH_2)$=NH may be carried out by known amidination methods, e.g. as described above at process step e).

The esterification of a compound of formula (I) wherein $R^2$ or $R^3$ is $CH_2OH$ in order to obtain compounds of formula (I) wherein $R^2$ or $R^3$ is —$CH_2OOCR^{10}$, wherein $R^{10}$ is as defined above, may be carried out in an analogous manner as in process step k).

The conversion of a compound of formula (I), in which $R^2$ or $R^3$ is —$CH_2OH$, into the corresponding compound of formula (I) wherein $R^2$ or $R^3$ is —$CH_2OPO(OH)_2$ can be performed as described above at process step i).

The conversion of a compound of formula (I), wherein $R^2$ or $R^3$ is —$COOR^6$ and in which $R^6$ is preferably methyl, into the corresponding compound of formula (I) wherein $R^2$ or $R^3$ is —$CONHR^7$ in which $R^7$ is phenyl or benzyl, can be carried out by aminolysis, e.g. as reported in Houben-Weyl, Vol. E5, page 983 (1985). Preferably the carbomethoxy compound is reacted with the amine compound of formula $H_2NPh$ or $H_2NCH_2Ph$ at reflux temperature by removing continuously the methanol formed by distillation.

Similarly the carbomethoxy compound can be reacted with a compound of formula

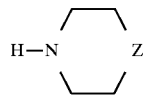

in which Z is as defined above, at reflux temperature by removing continuously the methanol formed by distillation, thus obtaining a compound of formula (I) in which one of $R^2$ and $R^3$ is

and the other is hydrogen.

The optional salification of a compound of formula (I) as well as the conversion of the salt into the free compound and the separation of a mixture of isomers into the single isomers may be carried out by conventional methods. For instance, the separation of a mixture of geometric isomers, e.g. cis- and trans-isomers, may be carried out by fractional crystallization from a suitable solvent or by chromatography, either column chromatography or high pressure liquid chromatography. The compounds of formula (II) may be obtained according to known methods from compounds of formula (IX)

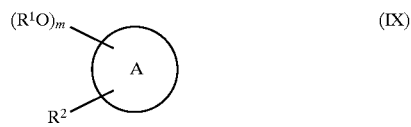

wherein A, $R^1$, $R^2$ and m are as defined above. E.g. the 3-formylindole compound of formula (II) wherein A is indole and $R^1$, $R^2$ and m are as defined above can be obtained from an indole compound of general formula (IX) by formylation with N-methylformanilide and $POCl_3$ according to the well known Vilsmeyer-Haak method (for a review see W. G. Jackson et al. in J. Am. Chem. Soc. 1981, 103, 533). The 2-formylindole derivatives are obtained when the 3-position is occupied.

In the case compound (IX) contains phenolic groups, i.e. $R^1O$ is hydroxy, the well known Reimer-Tiemann method can be applied. Thus the phenolic compound is treated with $CHCl_3$ and alkali hydroxides in an aqueous or hydroalcoholic solution. Another useful method for the synthesis of aromatic or phenolic aldehydes has been reported by H. Gross et al. in Chem. Ber. 1963, 96, 308. Accordingly a compound of formula (IX), in which the $OR^1$ group may be present or not, can be treated with 1,1-dichlorodimethylether in the presence of a Friedel-Crafts catalyst such as $TiCl_4$ or $AlCl_3$ in an inert solvent like $CH_2Cl_2$ or $PhNO_2$ at temperatures ranging from about 0° to 60° C.

The compounds of formula IV, V, VI VII and VIII can be obtained by condensation of a suitable 2-oxindole with a suitable compound of formula (II) according to process step a) as described above.

The compounds of formula (III) and (IX) are known or may be obtained by known methods from known compounds. When in the new compounds of the present invention and in the intermediate products used for their preparation there are groups present which need to be protected before the above-described reactions are performed, they may be protected before the reaction takes place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders.

Recent studies on the molecular basis or neoplastic transformation have identified a family of genes, designated oncogenes, whose aberrant expression causes tumorigenesis. For example, the RNA tumour viruses possess such an oncogene sequence whose expression determines neoplastic conversion of infected cells. Several of their oncogene-encoded proteins, such as pp60$^{v\text{-}src}$, p70$^{gag\text{-}yes}$, p130$^{gag\text{-}fps}$ and P70$^{gag\text{-}fgr}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptors tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiations and it can be effective in prevention and chemotherapy of cancer and other pathological proliferative conditions. Hence the compounds according to the present invention can be useful in the treatment of pathological proliferation disorders in mammals, including humans.

A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are benign and malignant tumours, including leukaemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyper-proliferation, such as psoriasis. The compounds of the invention can also be useful in inhibiting the development of the atheromatous plaque and restenosis, in the control of angiogenesis, as anti-metastatic agents and in treating diabetic complications. They have also utility in the control of immune system diseases, e.g. as immunosuppressants, as far as protein tyrosine kinases are involved in these diseases.

The tyrosine specific protein kinase activity of the compounds of the invention is shown, e.g., by the fact that they are active in the in vitro and in vivo test described herebelow.

In-vitro Assay p45 v-abl Kinase Purification

The enzyme used in our test was the p45 v-abl tyrosine kinase which represents the catalytic domain of the Abelson tyrosine kinase (isolated from the Abelson murine leukaemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

p45 v-abl Kinase Assay (Val$^5$)-Angiotension II phosphorylation was performed by incubation with 40 ng of purified abl-kinase and (γ-$^{32}$p)-ATP, in 50 μl of buffer containing Tris-HCl 25 mM, pH 8.0, MgCl$_2$ 10 mM and dithiothreitol 0.1 mM (kinase buffer). The reaction mixture was incubated for the indicated time at 30° C. and the reaction stopped by adding 50 μl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. IC$_{50}$ values were calculated from triplicated determinations of each experimental point. Each inhibitor was tested at concentrations ranging from 0 to 400 μg in the presence of fixed concentrations of peptide (2 Mm) and ATP (50 μM).

In-vivo Assay

K562 Cell Growth Inhibition Assay

K562 cells, a human myelogenous leukemia cell line, were seeded into a 24 wells tissue culture plate (Falcon 3047) (10000/well) in the presence of increasing concentrations of the compounds. After 72 h, cells were harvested and were counted using a cell counter (Coulter Counter—ZM). The percent of inhibition was evaluated in respect to the untreated control cells.

The inhibitory activity data for two representative compounds according to the present invention, obtained both in the in vitro p45 v-abl kinase assay and the in vivo human chronic myeloid leukemia K562 cell growth inhibition assay described above, are set out in the following Table I.

TABLE I

Inhibition of p45 v-abl kinase and K562 cell growth.

| Compound | IC$_{50}$ (μM) | |
|---|---|---|
| | v-abl | K562 |
| 5-(3-piperidinopropionylamino)-3-(5-methoxyindol-3-ylmethylene)-2-oxindole.HCl | 1.73 | 3.7 |
| 5-carboethoxy-3-(5-methoxyindol-3-ylmethylene)-2-oxindole | 1.99 | 2.34 |

As can be appreciated from the activity data shown in Table I, the compounds according to the invention are endowed with valuable biological properties.

In view of their high activity and low toxicity, the compounds of the invention can be used safely in medicine.

The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intramuscularly, or by intravenous injection of infusion; or topically. The dosage depends on the age, weight, condition of the patient and administration route. For example, the dosage adopted for oral administration to adult humans for the compound 5-sulfo-3-(3-hydroxytetralyl-2-ylmethylene)-2-oxindole may range from about 10 to about 150–200 mg per dose, from 1 to 5 times daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or filmcoating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering 1) a compound of the invention, or a pharmaceutically acceptable salt thereof, and
2) an additional antitumour agent, in amounts and close enough together in time sufficient to produce a therapeutically useful effect.

The present invention also provides products containing a compound of the invention, or a pharmaceutically acceptable salt thereof, and an additional antitumour agent as a combined preparation for simultaneous, separate or sequential use in anti-cancer therapy.

The term "antitumour agent" is meant to comprise both a single antitumour drug and "cocktails" i.e. a mixture of such drugs, according to the clinical practice.

Examples of antitumour agents that can be formulated with a compound of the invention or, alternatively, can be administered in a combined method of treatment, include doxorubicin, daunomycin, epirubicin, idarubicin, etoposide, fluorouracil, melphalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumour agent, for example an anthracycline glycoside such as doxorubicin, daunomycin, epirubicin or idarubicin as mentioned above, together with the antitumour agent.

A compound of the invention and an antitumour agent such as an anthracycline glycoside can be administered to improve the condition of a patient having a leukaemia such as myeloblastic leukaemia, lymphoma, sarcoma, neuroblastoma, Wilm's tumour or malignant neoplasm of the bladder, breast, lung or thyroid.

The following examples illustrate but do not limit the invention.

EXAMPLE 1

5-Sulfamoyl-3-(3-hydroxytetral-2-ylmethylene)-2-oxindole

A solution of 3-hydroxy-2-tetralinaldehyde (1.762 g, 10 mmol), 5-sulfamoyl-2-oxindole (1.802 g, 10 mmol) and piperidine (0.255 g, 3 mmol) in anhydrous ethanol (50 ml) was heated for 3 h at reflux. The reaction mixture was chilled to 5°–10° C., the precipitate filtered, the residue washed with ice-cold ethanol and then dried under vacuum. Almost pure title compound was so obtained in about 80% yield (2.707 g). Compounds of higher purity were obtained by crystallization from ethanol.

$C_{19}H_{18}N_2O_4$ calcd: C 61.61 H 4.90 N 7.56 S 8.66; found: C 61.55 H 4.85 N 7.51 S 8.55; MS m/z 370. IR $cm^{-1}$: 3500-2600 (NH, OH), 1700, 1695 (amide), 1600, 1580 (arom)

According to the above described procedure and starting from the appropriate compound of formula (II) and of formula (III), respectively, one can prepare the following compounds as single E- or Z-isomers, as well as their E,Z-mixtures:

5-sulfamoyl-3-[1,4-dihydroxytetral-2-ylmethylene]-2-oxindole;
5-sulfamoyl-3-[1-hydroxytetral-2-ylmethylene]-2-oxindole;
5-sulfamoyl-3-[3-hydroxytetral-2-ylmethylene]-2-oxindole;
5-sulfamoyl-3-[4-hydroxytetral-1-ylmethylene]-2-oxindole;
5-carbomethoxy-3-[1,4-dihydroxytetral-2-ylmethylene]-2-oxindole;
5-carbomethoxy-3-[3-hydroxytetral-2-ylmethylene]-2-oxindole;
5-[N,N-(4-hydroxyethyl)piperazinylcarbamyl]-3-[1,4-dihydroxytetral-2-ylmethylene]-2-oxindole;
5-diethanolamino-3-(1,4-dihydroxytetral-2-ylmethylene)-2-oxindole;
5-(2,3-dihydroxypropylamino)-3-(1,4-dihydroxytetral-2-ylmethylene)-2-oxindole;
5-ureido-3-(1,4-dihydroxytetral-2-ylmethylene)-2-oxindole;

5-guanidino-3-(1,4-dihydroxytetral-2-ylmethylene)-2-oxindole;
5-glyceroylamido-3-(1,4-dihydroxytetral-2-ylmethylene)-2-oxindole;
5-(3-piperidinopropionylamino)-3-(1,4-dihydroxytetral-2-ylmethylene)-2-oxindole;
5-mesylamino-3-(1,4-dihydroxytetral-2-ylmethylene)-2-oxindole;
5-glycoloyloxy-3-(1,4-dihydroxytetral-2-ylmethylene)-2-oxindole;
5-(2,3-dihydroxypropoxy)-3-(1,4-dihydroxytetral-2-ylmethylene)-2-oxindole;
5-aminomethyl-3-(1,4-dihydroxytetral-2-ylmethylene)-2-oxindole;
5-amidino-3-(1,4-dihydroxytetral-2-ylmethylene)-2-oxindole;
5-hydroxymethyl-3-(1,4-dihydroxytetral-2-ylmethylene)-2-oxindole;
5-sulfo-3-(quinol-4-ylmethylene)-2-oxindole;
5-sulfamoyl-3-(quinol-4-ylmethylene)-2-oxindole;
5-carbomethoxy-3-(quinol-4-ylmethylene)-2-oxindole;
5-diethanolamino-3-(quinol-4-ylmethylene)-2-oxindole;
5-(2,3-dihydroxypropylamino)-3-(quinol-4-ylmethylene)-2-oxindole;
5-ureido-3-(quinol-4-ylmethylene)-2-oxindole;
5-guanidino-3-(quinol-4-ylmethylene)-2-oxindole;
5-glyceroylamido-3-(quinol-4-ylmethylene)-2-oxindole;
5-(3-piperidinopropionylamino)-3-(quinol-4-ylmethylene)-2-oxindole;
5-mesylamino-3-(quinol-4-ylmethylene)-2-oxindole;
5-glycoloyloxy-3-(quinol-4-ylmethylene)-2-oxindole;
5-(2,3-dihydroxypropoxy)-3-(quinol-4-ylmethylene)-2-oxindole;
5-aminomethyl-3-(quinol-4-ylmethylene)-2-oxindole;
5-amidino-3-(quinol-4-ylmethylene)-2-oxindole;
5-hydroxymethyl-3-(quinol-4-ylmethylene)-2-oxindole;
5-sulfamoyl-3-(indol-3-ylmethylene)-2-oxindole;
5-carbomethoxy-3-(indol-3-ylmethylene)-2-oxindole;
5-diethanolamino-3-(indol-3-ylmethylene)-2-oxindole;
5-(2,3-dihydroxypropylamino)-3-(indol-3-ylmethylene)-2-oxindole;
5-ureido-3-(indol-3-ylmethylene)-2-oxindole;
5-guanidino-3-(indol-3-ylmethylene)-2-oxindole;
5-glyceroylamido-3-(indol-3-ylmethylene)-2-oxindole;
5-(3-piperidinopropionylamino)-3-(indol-3-ylmethylene)-2-oxindole;
5-mesylamino-3-(indol-3-ylmethylene)-2-oxindole;
5-glycoloyloxy-3-(indol-3-ylmethylene)-2-oxindole;
5-(2,3-dihydroxypropoxy)-3-(indol-3-ylmethylene)-2-oxindole;
5-aminomethyl-3-(indol-3-ylmethylene)-2-oxindole;
5-amidino-3-(indol-3-ylmethylene)-2-oxindole;
5-hydroxymethyl-3-(indol-3-ylmethylene)-2-oxindole;
3-(5-sulfamoylindol-3-ylmethylene)-2-oxindole;
3-(5-carbomethoxyindol-3-ylmethylene)-2-oxindole;
  $C_{19}H_{14}N_2O_3$ calcd: C 71.69 H 4.43 N 8.80; found: C 71.55 H 4.45 N 8.75; MS m/Z 318; NMP δ ppm (DMSO-d): 3.89 (s, 3H), 6.82 (d, 1H, J=7.5 Hz), 6.95 (ddd, 1H, J=7.5/7.5/1.1 Hz), 7.14 (ddd, 1H, J=7.5/7.5/1.1 Hz), 7.58 (d, 1H, J=8.6 Hz), 7.85 (dd, 1H, J=8.6/1.6 Hz), 8.01 (d, 1H, J=7.5 Hz), 8.23 (s, 1H), 8.87 (d, 1H, J=1.6 Hz), 9.51 (s, 1H), 10.53 (bs, 1H), 12.2 (bs, 1H)
3-(5-diethanolamino-3-indolylmethylene)-2-oxindole;
3-[5-(2,3-dihydroxypropylamino)-3-indolylmethylene]-2-oxindole;
3-(5-ureido-3-indolylmethylene)-2-oxindole;
3-(5-guanidino-3-indolylmethylene)-2-oxindole;
3-(5-glyceroylamido-3-indolylmethylene)-2-oxindole;
3-[5-(3-piperidinopropionylamino)-3-indolylmethylene]-2-oxindole;
3-(5-mesylamino-3-indolylmethylene)-2-oxindole;
3-(5-glycoloyloxy-3-indolylmethylene)-2-oxindole;
3-[5-(2,3-dihydroxypropoxy)-3-indolylmethylene]-2-oxindole;
3-(5-aminomethyl-3-indolylmethylene)-2-oxindole;
3-(5-amidino-3-indolylmethylene)-2-oxindole;
3-(5-hydroxymethyl-3-indolylmethylene)-2-oxindole;
5-sulfamoyl-3-(naphth-2-ylmethylene)-2-oxindole;
5-carbomethoxy-3-(naphth-2-ylmethylene)-2-oxindole;
5-diethanolamino-3-(naphth-2-ylmethylene)-2-oxindole;
5-(2,3-dihydroxypropylamino)-3-(naphth-2-ylmethylene)-2-oxindole;
5-ureido-3-(naphth-2-ylmethylene)-2-oxindole;
5-guanidino-3-(naphth-2-ylmethylene)-2-oxindole;
5-glyceroylamido-3-(naphth-2-ylmethylene)-2-oxindole;
5-(3-piperidinopropionylamino)-3-(naphth-2-ylmethylene)-2-oxindole;
5-mesylamino-3-(naphth-2-ylmethylene)-2-oxindole;
5-glycoloyloxy-3-(naphth-2-ylmethylene)-2-oxindole;
5-(2,3-dihydroxypropoxy)-3-(naphth-2-ylmethylene)-2-oxindole;
5-aminomethyl-3-(naphth-2-ylmethylene)-2-oxindole;
5-amidino-3-(naphth-2-ylmethylene)-2-oxindole;
5-hydroxymethyl-3-(naphth-2-ylmethylene)-2-oxindole;
5-sulfo-3-(1-hydroxytetral-2-ylmethylene)-2-oxindole, sodium salt;
  $C_{19}H_{16}NO_5SNa$ calcd: C 58.01 H 4.10 N 3.56 S 8.15 Na 5.83; found: C 57.95 H 4.15 N 3.45 S 8.05 Na 5.79; MS m/Z 393. NMR δ ppm (DMSO): 1.5–1.8 (m, 4H), 2.5–2.9 (m, 4H), 6.66 (d, J=8.0 Hz, 1H), 6.75 (d, J=8.2 Hz, 1H), 7.32 (d, J=8.0 Hz, 1H), 7.44 (dd, J=8.2 and 1.5 Hz, 1H), 6.69 (s, 1H), 7.89 (d, J=1.5 Hz, 1H), 10.6 (bs, 1H).
5-sulfo-3-(4-hydroxytetral-2-ylmethylene)-2-oxindole, sodium salt
  $C_{19}H_{16}NO_5SNa$ calcd: C 58.01 H 4.10 N 3.56 S 8.15 Na 5.83; found: C 57.85 H 4.05 N 3.55 S 8.10 Na 5.69; MS m/z 393. NMR δ ppm (DMSO): 1.6–1.8 (m, 4H), 2.4–2.8 (m, 4H), 6.70 (d, J=8.5 Hz, 1H), 6.75 (d, J=7.9 Hz, 1H), 7.29 (d, J=8.5 Hz, 1H), 7.43 (dd, J=7.9 and 1.5 Hz, 1H), 7.60 (s, 1H), 7.79 (d, J=1.5 Hz, 1H), 10.6 (bs, 1H).
(E,Z)-5-(3-piperidinopropionylamino)-3-(5-methoxyindol-3-ylmethylene)-2-oxindole, hydrochloride salt
  $C_{26}H_{29}ClN_4O_3$ calcd: C 64.93 H 6.08 Cl 7.37 N 11.65 C 64.85 H 5.95 Cl 7.25 N 11.58; MS m/z 481. NMR δ ppm (DMSO): 1.2–2.0 (m, $6H_E$, $6H_Z$), 2.8–3.6 (m, $8H_E$, $8H_Z$), 3.88 (s, $3H_Z$), 3.82 (s, $3H_E$), 6.7–7.0 (m, $2H_E$, $2H_Z$), 7.20 (d, J=2.3 Hz, $1H_E$), 7.20–7.5 (m, $2H_E$, $2H_Z$), 7.57 (d, J=2.3 Hz, $1H_Z$), 7.86 (s, $1H_E$), 7.80 (d, J=1.7 Hz, $1H_Z$), 7.99 (s, $1H_Z$), 8.17 (d, J=3.0 Hz, $1H_E$), 8.31 (d, J=1.7 Hz, $1H_E$), 9.42 (d, J=3.0 Hz, $1H_Z$), 9.8 (bs, $1H_E$, $1H_Z$).
3-[5-(p-chlorophenyl)sulfonylamidoindol-3-yl-methylene]-2-oxindole
  $C_{23}H_{16}ClN_3O_3S$ calcd: C 61.40 H 3.59 Cl 7.88 S 7.13; found: C 61.38 H 3.56 Cl 7.55 S 7.05; MS m/z 449. NMR δ ppm (DMSO): 6.82 (m, 2H), 7.00 (m, 1H), 7.15 (m, 1H), 7.36 (d, J=8.6 Hz, 1H), 7.5–7.8 (m, 4H), 7.80 (m, 2H), 7.93 (s, 1H), 9.40 (d, J=2.9 Hz, 1H), 10.0 (bs, 1H), 10.52 (s, 1H), 12.01 (d, J=2.9 Hz, 1H).
5-carboethoxy-3-(3-hydroxytetral-2-ylmethylene)-2-oxindole;
5-carboethoxy-3-(quinol-4-ylmethylene)-2-oxindole;
5-carboethoxy-3-(5-methoxyindol-3-ylmethylene)-2-oxindole;
  $C_{21}H_{18}N_2O_4$ calcd: C 69.60 H 5.01 N 7.73; found: C 69.55 H 4.95 N 7.65; MS m/z 362. NMR δ ppm (DMSO-$d_6$):

1.34 (t, 3H, J=7.2 Hz), 3.88 (s, 3H), 4.32 (t, 2H, J=7.2 Hz), 6.85 (dd, 1H, J=8.6 and 2.4 Hz), 6.92 (d, 1H, J=8.4 Hz), 7.39 (d, 1H, J=8.6 Hz), 7.78 (dd, 1H, J=8.4 and 1.5 Hz), 7.83 (d, 1H, J=2.4 Hz), 8.32 (s, 1H), 8.49 (d, 1H, J=1.5 Hz), 9.45 (s, 1H), 10.89 (bs, 1H), 12.0 (bs, 1H);

3-(5-carboethoxyindol-3-ylmethylene)-2-oxindole;
5-carbobenzyloxy-3-(3-hydroxytetral-2-ylmethylene)-2-oxindole;
5-carbobenzyloxy-3-(quinol-4-ylmethylene)-2-oxindole;
5-carbobenzyloxy-3-(5-methoxyindol-3-ylmethylene)-2-oxindole;
3-(5-carbobenzyloxyindol-3-ylmethylene)-2-oxindole;
5-phenylcarbamoyl-3-(3-hydroxytetral-2-ylmethylene)-2-oxindole;
5-phenylcarbamoyl-3-(quinol-4-ylmethylene)-2-oxindole;
5-phenylcarbamoyl-3-(5-methoxyindol-3-ylmethylene)-2-oxindole;
3-(5-phenylcarbamoylindol-3-ylmethylene)-2-oxindole;
5-benzylcarbamoyl-3-(3-hydroxytetral-2-ylmethylene)-2-oxindole;
5-benzylcarbamoyl-3-(quinol-4-ylmethylene)-2-oxindole;
5-benzylcarbamoyl-3-(5-methoxyindol-3-ylmethylene)-2-oxindole;

$C_{26}H_{21}N_3O_3$ calcd: C 73.74 H 5.00 N 9.92; found: C 73.71 H 4.99 N 9.85; MS m/z 423. NMR δ ppm (DMSO-$d_6$): 3.86 (s, 3H), 4.51 (d, 2H, J=5.9 Hz), 6.85 (m, 2H), 7.1–7.5 (m, 6H), 7.70 (m, 2H), 8.19 (s, 1H), 8.38 (d, 1H, J=1.5 Hz), 8.84 (t, 1H, J=5.9 Hz), 9.42 (s, 1H), 10.75 (bs, 1H), 12.0 (bs, 1H);

3-(5-benzylcarbamoylindol-3-ylmethylene)-2-oxindole;
5-carboethoxy-3-(8-hydroxyquinol-5-ylmethylene)-2-oxindole;
5-benzylcarbamoyl-3-(8-hydroxyquinol-5-ylmethylene)-2-oxindole; and
5-sulfo-3-(5-methoxyindol-3-ylmethylene)-2-oxindole, MS m/z 370; NMR δ ppm (DMSO): 3.88 (s, 3H), 6.73 (d, 1H, J=8.1 Hz), 6.81 (dd, 1H, J=8.6 and 2.4 Hz), 7.37 (d, 1H, J=8.6 Hz), 7.43 (dd, 1H, J=8.1 and 1.8 Hz), 7.74 (d, 1H, J=2.4 Hz), 8.08 (d, 1H, J=1.8 Hz), 8.14 (s, 1H), 9.43 (s, 1H), 10.51 (bs, 1H), 11.8 (bs, 1H);

5-amidino-3-(5-methoxyindol-3-ylmethylene)-2-oxindole hydrochloride,

MS m/z 368. $C_{19}H_7ClN_4O_2$ calcd: C 61.87 H 4.65 Cl 9.61 N 15.19; found: C 61.55 H 4.55 Cl 9.55 N 15.01.

EXAMPLE 2

5-Sulfo-3-(3-hydroxytetral-2-ylmethylene)-2-oxindole

A solution of 3-hydroxy-2-tetralinaldehyde (1.762 g, 10 mmol) and 2-oxindole-5-sulfonic acid (2.559 g, 12 mmol) in anhydrous ethanol (10 ml) was heated to reflux for 1 hour. The reaction mixture was chilled with ice water, the precipitate filtered, the residue washed with ice-cooled ethanol and dried under vacuum. Almost pure title compound was obtained in about 70% yield (2.600 g).

$C_{19}H_{17}NO_5S$ calcd: C 61.44 H 4.61 N 3.77 S 8.63; found: C 61.35 H 4.45 N 3.71 S 8.65; MS m/z 371. IR cm$^{-1}$: 3500-2500 (NH, OH), 1690, 1630 (amide), 1600 (arom).

According to the above described procedure and starting from the appropriate compound of formula (II) and formula (III), respectively, one can prepare the following compounds as single E- or Z-isomers, as well as their E,Z-mixtures:
5-sulfo-3-(1,4-dihydroxytetral-2-ylmethylene)-2-oxindole;
5-sulfo-3-(1-hydroxytetral-2-ylmethylene)-2-oxindole;
5-sulfo-3-(4-hydroxytetral-1-ylmethylene)-2-oxindole;
5-sulfo-3-(quinol-4-ylmethylene)-2-oxindole;
5-sulfo-3-(indol-3-ylmethylene)-2-oxindole;
3-(5-sulfoindol-3-ylmethylene)-2-oxindole;
5-sulfo-3-(naphth-2-ylmethylene)-2-oxindole;
5-phosphonooxy-3-(1,4-dihydroxytetral-2-ylmethylene)-2-oxindole;
5-phosphonooxy-3-(quinol-4-ylmethylene)-2-oxindole;
5-phosphonooxy-3-(indol-3-ylmethylene)-2-oxindole;
3-(5-phosphonooxy-3-indolylmethylene)-2-oxindole; and
5-phosphonooxy-3-(naphth-2-ylmethylene)-2-oxindole.

EXAMPLE 3

5-(2,3-dihydroxypropylamino)-3-(quinol-4-ylmethylene)-2-oxindole

To a stirred solution of 5-amino-3-(quinol-4-ylmethylene)-2-oxindole (2.873 g, 10 mmol) in methanol (30 ml) was added anhydrous methylammonium chloride (0.60 g, 10 mmol). Then sodium cyanoborohydride (0.378 g, 6 mmol) was added in portions. Finally, glyceraldehyde (0.901 g, 10 mmol) was added portionwise over 30 min and the solution stirred at r.t. for 50 h. Ice cold 6N HCl was added until gas evolution (HCN) stopped and the pH of the solution was 2. The methanol was evaporated in vacuo and the remaining aqueous solution was washed with $CHCl_3$. Solid KOH was added until the pH was 12. Solid NaCl was added to saturation and the solution extracted twice with $CHCl_3$. The $CHCl_3$ extracts were washed with saturated NaCl solution, dried over $K_2CO_3$ and evaporated. The residue was chromatographed on silica gel using $CHCl_3$-MeOH mixtures as eluant.

Thus pure title compound was obtained in about 60% yield.

$C_{21}H_{19}N_3O_3$ calcd: C 69.79 H 5.30 N 11.63; found: C 69.75 H 5.25 N 11.55; MS m/z 361. IR cm$^{-1}$: 3500-2500 (NH, OH), 1700, 1640, 1620 (amide), 1600, 1580 (arom).

According to the above described procedure, the following compounds can be prepared:
5-(2,3-dihydroxypropylamino)-3-(1,4-dihydroxytetral-2-ylmethylene)-2-oxindole;
5-(2,3-dihydroxypropylamino)-3-(indol-3-ylmethylene)-2-oxindole;
3-[5-(2,3-dihydroxypropylamino)-3-indolylmethylene]-2-oxindole;
5-(2,3-dihydroxypropylamino)-3-(naphth-2-ylmethylene]-2-oxindole; and
(E,Z)-5-(2,3-dihydroxypropylamino)-3-(5-methoxy-3-indolylmethylene)-2-oxindole, MS m/z 379. NMR δ ppm (DMSO): 2.7–3.3 (m,$2H_E$+$2H_Z$), 3.5–3.8 (m, $1H_E$+$1H_Z$), 3.80, 3.86 (2 singlets, $3H_E$+$3H_Z$), 4.5–5.2 (bs, $3H_E$+$3H_Z$), 6.45 (m, $1H_E$+$1H_Z$), 6.58, 6.62 (two d, $1H_E$+$1H_Z$, J=6.8 and 6.8 Hz), 6.85 (m, $1H_E$+$1H_Z$), 7.13 (d, $1H_E$, J=2.2 Hz), 7.18 (d, $1H_Z$, J=2.2 Hz), 7.23 (d, $1H_E$, J=2.2 Hz), 7.40 (two d, $1H_E$+$1H_Z$, J=8.7 and 8.8 Hz), 7.62 (d, $1H_Z$, J=2.6 Hz), 7.76 (s, $1H_E$), 7.94 (s, $1H_Z$), 8.17 (s, $1H_E$), 9.38 (s, $1H_Z$), 10.00, 10.05 (two s, $1H_E$+$1H_Z$), 11.7–12.1 (bs, $1H_E$+$1H_Z$).

EXAMPLE 4

5-glyceroylamido-3-(quinol-4-ylmethylene)-2-oxindole

To a stirred solution of 5-amino-3-(quinol-4-ylmethylene)-2-oxindole (2.873 g, 10 mmol) and glyceric acid (1.061 g, 10 mmol) was added dicyclohexylcarbodiimide (2.063 g, 10 mmol). The resulting suspension was stirred for 1 hour at 50°–60° C. and then for 3 days at room temperature. Then the N,N'-dicyclohexylurea was filtered off, the filtrate evaporated and the residue chromatographed on silica gel using $CHCl_3$—MeOH mixtures as eluant. Thus pure title compound was obtained in about 60% yield.

$C_{21}H_{17}N_3O_4$ calcd: C 67.19 H 4.57 N 11.19; found: C 67.13 H 4.46 N 11.07; MS m/z 375. IR cm$^{-1}$: 3500–2500 (NH, OH), 1700, 1680, 1620 (amide)

According to the above described procedure, the following compounds can be prepared:
5-glyceroylamido-3-(indol-3-ylmethylene)-2-oxindole;
3-(5-glyceroylamido-3-indolylmethylene)-2-oxindole; and
5-glyceroylamido-3-(naphth-3-ylmethylene)-2-oxindole.

EXAMPLE 5

5-mesylamino-3-(quinol-4-ylmethylene)-2-oxindole

To a stirred solution of 5-amino-3-(quinol-4-ylmethylene)-2-oxindole (2.873 g, 10 mmol) in pyridine (10 ml) was added gradually mesylchloride (1.146 g, 10 mmol) at 0°–5° C. under cooling. The reaction mixture was stirred for about 5 h at 0°–5° C. and then for 15 hours at room temperature. The mixture was poured onto an ice-water mixture, the precipitate filtered off, the residue washed thoroughly with water and then chromatographed on silica gel using $CHCl_3$—MeOH mixtures as eluant. Thus pure title compound was obtained in about 70% yield.

$C_{19}H_{15}N_3O_3S$ calcd: C 62.45 H 4.14 N 11.50 S 8.77; found: C 62.39 H 4.15 N 11.38 S 8.73; MS m/z 365. IR cm$^{-1}$: 3600–3000 (NH), 1710, 1630, 1620 (amide).

By proceeding analogously, the following compounds can be prepared:
5-mesylamino-3-(indol-3-ylmethylene)-2-oxindole;
3-(5-mesylamino-3-indolylmethylene)-2-oxindole; and
5-mesylamino-3-(naphth-2-ylmethylene)-2-oxindole.

EXAMPLE 6

5-guanidino-3-(quinol-4-ylmethylene)-2-oxindole

A mixture of 5-amino-3-(quinol-4-ylmethylene)-2-oxindole (2.873 g, 10 mmol) and sodium bicarbonate (0.168 g, 2 mmol) in refluxing ethanol (100 ml) was treated with 3,5-dimethylpyrazole-1-carboxamidine nitrate (3.018 g, 15 mmol) for 20 h. The solvent was removed from the cooled solution, and the residue was chromatographed on silica gel with gradient elution (1 to 5% EtOH in $CHCl_3$) to afford pure title compound in about 50% yield.

$C_{19}H_{15}N_5O$ calcd: C 69.29 H 4.59 N 21.26; found: C 69.21 H 4.45 N 21.15; MS m/Z 3 29. IR cm$^{-1}$: 3500–2500 (NH), 1700 (amide), 1680 (C=NH), 1620 (amide), 1580 (arom).

According to the above described procedure, the following compounds can be prepared:
5-guanidino-3-(indol-3-ylmethylene)-2-oxindole;
3-(5-guanidino-3-indolylmethylene)-2-oxindole; and
5-guanidino-3-(naphth-2-ylmethylene)-2-oxindole.

EXAMPLE 7

5-ureido-3-(quinol-4-ylmethylene)-2-oxindole

To a mixture of 5-amino-3-(quinol-4-ylmethylene)-2-oxindole (2.873 g, 10 mmol) in ice water (20 ml) was added 5N HCl (2 ml, 10 mmol) under stirring. Then the mixture was heated to 70°–80° C., sodium cyanate (0.715 g, 11 mmol) was added portionwise and the stirring was continued for further 4 h at this temperature. After cooling, the raw product was extracted with $CHCl_3$, the organic layer washed to neutrality with saline solution, dried and evaporated in vacuo. The residue was chromatographed on silica gel, using $CHCl_3$—MeOH mixtures as eluant to give pure title compound in about 50% yield.

$C_{19}H_{14}N_4O_2$ calcd: C 69.08 H 4.27 N 16.96; found: C 69.01 H 4.15 N 16.85; MS m/z 330. IR cm$^{-1}$: 3500–2500 (NH), 1705, 1660, 1640, 1620 (amide), 1580 (arom).

By proceeding analogously, the following compounds can be prepared:
5-ureido-3-(indol-3-ylmethylene)-2-oxindole;
3-(5-ureido-3-indolylmethylene)-2-oxindole; and
5-ureido-3-(naphth-2-ylmethylene)-2-oxindole.

EXAMPLE 8

5-(2,3-dihydroxypropoxy)-3-(quinol-4-ylmethylene)-2-oxindole

To a solution of 5-hydroxy-3-(quinol-4-ylmethylene)-2-oxindole (2.883 g, 10 mmol) in toluene (100 ml) was added portionwise under nitrogen NaH 80% (0.300 g, 10 mmol). After salification was complete, 3-chloro-1,2-propanediol (1.547 g, 14 mmol) was added and the mixture heated to reflux for 5 h. After cooling, water was added, the organic phase washed and evaporated to dryness. The residue was submitted to flash chromatography, using $CHCl_3$—MeOH mixtures as eluant to give pure title compound in about 70% yield.

$C_{21}H_{18}N_2O_4$ calcd: C 69.60 H 5.01 N 7.73; found: C 69.55 H 4.95 N 7.65; MS m/z 362. IR cm$^{-1}$: 3500–2600 (NH, OH), 1700, 1640 (amide), 1600, 1580 (arom).

By proceeding analogously, the following compounds can be prepared:
5-(2, 3-dihydroxypropoxy)-3-(indol-3-ylmethylene)-2-oxindole;
3-[5-(2,3-dihydroxypropoxy)-3-indolylmethylene]-2-oxindole; and
5-(2,3-dihydroxypropoxy)-3-(naphth-2-ylmethylene)-2-oxindole.

EXAMPLE 9

5-glycoloyloxy-3-(quinol-4-ylmethylene)-2-oxindole

To a stirred solution of 5-hydroxy-3-(quinol-4-ylmethylene)-2-oxindole (2.883 g, 10 mmol) in pyridine (10 ml) was added gradually glycoloyl chloride (0.945 g, 10 mmol) at 0°–5° C. under cooling. The reaction mixture was stirred for about 4 h at 0°–5° C. and then for 15 h at room temperature. The mixture was poured onto an ice-water mixture, the precipitate filtered off, the residue washed thoroughly with water and then chromatographed on silica gel, using $CHCl_3$—MeOH mixtures as eluant. Thus pure title compound was obtained in about 60% yield.

$C_{20}H_{14}N_2O_4$ calcd: C 69.36 H 4.07 N 8.09; found: C 69.31 H 4.01 N 7.95; MS m/z 346. IR cm$^{-1}$: 3500–2600 (NH, OH), 1740 (ester), 1700, 1640 (amide), 1600, 1580 (arom).

In analogous manner, the following compounds can be obtained:
5-glycoloyloxy-3-(indol-3-ylmethylene)-2-oxindole;
3-(5-glycoloyloxy-3-indolylmethylene)-2-oxindole; and
5-glycoloyloxy-3-(naphth-2-ylmethylene)-2-oxindole.

EXAMPLE 10

5-phosphonooxy-3-(quinol-4-ylmethylene)-2-oxindole

A mixture of 5-hydroxy-3-(quinol-4-ylmethylene)-2-oxindole (2.883 g, 10 mmol) and phosphoric acid 85% (13 g) and phosphorous pentoxide (10 g) was heated for 2 h at 60° C. The usual work-up gave the title compound in about 50% yield.

$C_{18}H_{13}N_2O_5P$ calcd: C 58.71 H 3.56 N 7.61 P 8.41; found: C 58.65 H 3.51 N 7.45 P 8.35; MS m/z 368. IR cm$^{-1}$: 3500–2500 (OH), 1700, 1640, 1620 (amide), 1600, 1580 (arom).

According to the above described procedure, the following compounds can be obtained:
5-phosphonooxy-3-(indol-3-ylmethylene)-2-oxindole;
3-(5-phosphonooxy-3-indolylmethylene)-2-oxindole; and
5-phosphonooxy-3-(naphth-2-ylmethylene)-2-oxindole.

EXAMPLE 11

5-carbomethoxy-3-(quinol-4-ylmethylene)-2-oxindole

A solution of 5-carboxy-3-(quinol-4-ylmethylene)-2-oxindole (3.163 g, 10 mmol), methanol (3.2 g, 100 mmol) and $H_2SO_4$ 95% (1 g) in benzene (100 ml) was heated in a Soxhlet apparatus for 10 h. To dry the distillate continuously, the cap of the Soxhlet contained anhydrous $MgSO_4$. After cooling, water was added, the organic phase repeatedly washed with water and then evaporated under vacuum. Thus almost pure title compound was obtained in about 90% yield.

$C_{20}H_{14}N_2O_3$ calcd: C 72.72 H 4.27 N 8.48; found: C 72.65 H 4.23 N 8.35; MS m/z 330. IR cm$^{-1}$: 3500-2500 (NH), 1720 (ester), 1700, 1640 (amide), 1600, 1580 (arom).

By proceeding analogously, the following compounds can be obtained:
5-carbomethoxy-3-(1,4-dihydroxytetral-2-ylmethylene)-2-oxindole;
5-carbomethoxy-3-(3-hydroxytetral-2-ylmethylene)-2-oxindole;
5-carbomethoxy-3-(indol-3-ylmethylene)-2-oxindole;
3-(5-carbomethoxyindol-3-ylmethylene)-2-oxindole; and
5-carbomethoxy-3-(naphth-2-ylmethylene)-2-oxindole.

EXAMPLE 12

5-amidino-3-(quinol-4-ylmethylene)-2-oxindole, hydrochloride salt

To a solution of 5-cyano-3-(quinol-4-ylmethylene)-2-oxindole (2.973 g, 10 mmol) in anhydrous diethyl ether (100 ml), a stoichiometric amount of ethanol (0.460 g, 10 mmol) was added and the solution was saturated with HCl gas. The solution was kept overnight in the fridge in order to precipitate the iminoether hydrochloride salt. The precipitated iminoether hydrochloride was dissolved in ethanol (50 ml) to which was added an anhydrous alcoholic ammonia solution. Thereupon, the solution was kept several days at room temperature and the precipitated little amount of $NH_4Cl$ was filtered off. The solution was evaporated in vacuum, thus obtaining almost pure title compound.

$C_{19}H_{14}N_4O \cdot HCl$ calcd: C 65.05 H 4.31 N 15.97 Cl 10.11; found: C 65.01 H 4.25 N 15.85 Cl 10.05; MS m/z 350.

The following compounds can be obtained following the above described method:
5-amidino-3-(indol-3-ylmethylene)-2-oxindole hydrochloride;
5-amidino-3-(5-methoxyindol-3-ylmethylene)-2-oxindole hydrochloride;
3-(5-amidino-3-indolylmethylene)-2-oxindole hydrochloride; and
5-amidino-3-(naphth-2-ylmethylene)-2-oxindole hydrochloride.

EXAMPLE 13

5-aminomethyl-3-(quinol-4-ylmethylene)-2-oxindole

To a solution of 5-chloromethyl-3-(quinol-4-ylmethylene)-2-oxindole (3.208 g, 10 mmol) in $CHCl_3$ (50 ml) was added a solution of hexamethylenetetramine (1.402 g, 10 mmol) in $CHCl_3$ (20 ml) at 40°–50° C. The resulting quaternary salt was filtered off after cooling. The crystalline residue was then dissolved in a mixture of ethanol (5.5 g, 120 mmol) and HCl 32% (3 ml, 30 mmol) and the diethoxymethane formed was eliminated by distillation. The latter operation was repeated twice. After alkalinization with diluted soda solution, the raw product was extracted with $CHCl_3$ the organic layer washed to neutrality, dried and evaporated. The residue was submitted to column chromatography on silica gel, using a $CHCl_3$—EtOH mixture as eluant, thus giving pure title compound in 65% yield.

$C_{19}H_{15}N_3O$ calcd: C 75.73 H 5.02 N 13.94; found: C 75.65 H 4.95 N 13.89; MS m/z 301. IR cm$^{-1}$: 3500-2600 (NH), 1695, 1640, 1620 (amide), 1580 (arom).

The following compounds are obtained by proceeding analogously:
5-aminomethyl-3-(indol-3-ylmethylene)-2-oxindole;
3-(5-aminomethyl-3-indolylmethylene)-2-oxindole; and
5-aminomethyl-3-(naphth-2-ylmethylene)-2-oxindole.

EXAMPLE 14

5-sulfo-3-(3-hydroxytetral-2-ylmethylene)-2-oxindole, sodium salt

To a solution of 5-sulfo-3-(3-hydroxytetral-2-ylmethylene)-2-oxindole (3.714 g, 10 mmol) in 1N NaOH (10 ml, 10 mmol) was added isopropanol (30 ml) and the mixture was chilled under stirring to 0°–5° C. The precipitated sodium salt was filtered, washed with ice-cooled isopropanol and dried under vacuum.

$C_{19}H_{16}NO_5SNa$ calcd: C 58.01 H 4.10 N 3.56 S 8.15 Na 5.85; found: C 57.95 H 4.05 N 3.45 S 8.20 Na 5.75; MS m/z 393.

The following salt can be obtained in an analogous manner:
5-sulfo-3-(1,4-dihydroxytetral-2-ylmethylene)-2-oxindole, sodium salt;
5-sulfo-3-(quinol-4-ylmethylene)-2-oxindole, sodium salt;
5-sulfo-3-(indol-3-ylmethylene)-2-oxindole, sodium salt;
3-(5-sulfoindol-3-ylmethylene)-2-oxindole, sodium salt;
5-sulfo-3-(naphth-2-ylmethylene)-2-oxindole, sodium salt;
5-sulfo-3-(1-hydroxytetral-2-ylmethylene)-2-oxindole, sodium salt.

$C_{19}H_{16}NO_5SNa$ calcd: C 58.01 H 4.10 N 3.56 S 8.15 Na 5.83; found: C 57.95 H 4.15 N 3.45 S 8.05 Na 5.79; MS m/z 393. NMR δ ppm (DMSO): 1.5–1.8 (m, 4H), 2.5–2.9 (m, 4H), 6.66 (d, J=8.0 Hz, 1H), 6.75 (d, J=8.2 Hz, 1H), 7.32 (d, J=8.0 Hz, 1H), 7.44 (dd, J=8.2 and 1.5 Hz, 1H), 6.69 (s, 1H), 7.89 (d, J=1.5 Hz, 1H), 10.6 (bs, 1H).

5-sulfo-3-(4-hydroxytetral-2-ylmethylene)-2-oxindole, sodium salt;

$C_{19}H_{16}NO_5SNa$ calcd: C 58.01 H 4.10 N 3.56 S.8.15 Na 5.83; found: C 57.85 H 4.05 N 3.55 S 8.10 Na 5.69; MS m/z 393. NMR δ ppm (DMSO): 1.6–1.8 (m, 4H), 2.4–2.8 (m, 4H), 6.70 (d, J=8.5 Hz, 1H), 6.75 (d, J=7.9 Hz, 1H), 7.29 (d, J=8.5 Hz, 1H), 7.43 (dd, J=7.9 and 1.5 Hz, 1H), 7.60 (s, 1H), 7.79 (d, J=1.5 Hz, 1H), 10.6 (bs, 1H).

EXAMPLE 15

5-aminomethyl-3-(quinol-4-ylmethylene)-2-oxindole, hydrochloride salt

To a solution of 5-aminomethyl-3-(quinol-4-ylmethylene)-2-oxindole (3.014 g, 10 mmol) in ethanol (10 ml) was added 1N hydrochloric acid (2 ml, 2 mmol) and the resulting mixture was evaporated to dryness under vacuum, thus giving pure title compound in about 100% yield.

$C_{19}H_{17}N_3OCl_2$ calcd: C 60.97 H 4.58 N 11.23 Cl 18.95; found: C 60.85 H 4.45 N 11.15 Cl 18.90; MS m/x 374.

EXAMPLE 16

Tablets each weighing 0.150 g and containing 25 mg of the active substance, can be manufactured as follows:
Composition (for 10,000 tablets):

| | |
|---|---|
| 5-sulfo-3-(3-hydroxytetral-2-ylmethylene)-2-oxindole | 250 g |
| Lactose | 800 g |
| Corn starch | 415 g |
| Talc powder | 30 g |
| Magnesium stearate | 5 g |

The 5-sulfo-3-(3-hydroxytetral-2-ylmethylene)-2-oxindole, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 17

Capsules, each dosed at 0.200 g and containing 20 mg of the active substance can be prepared.
Composition for 500 capsules:

| | |
|---|---|
| 5-sulfamoyl-3-(3-hydroxytetral-2-ylmethylene)-2-oxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

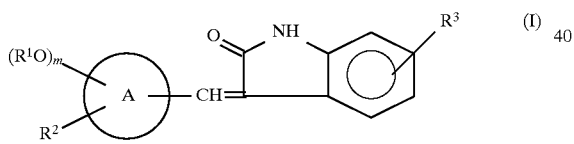

wherein
m is zero, 1 or 2;
A is a bicyclic ring selected from the group consisting of tetralin, naphthalene, quinoline and indole;
$R^1$ is hydrogen, $C_1$–$C_6$ alkyl or $C_2$–$C_6$ alkanoyl; one of $R^2$ and $R^3$ independently is hydrogen and the other is a substituent selected from the group consisting of:
a $C_1$–$C_6$ alkyl group substituted by 1, 2 or 3 hydroxy groups;
—$SO_3R^4$ in which $R^4$ is hydrogen or $C_1$–$C_6$ alkyl unsubstituted or substituted by 1, 2 or 3 hydroxy groups;
—$SO_2NHR^5$ in which $R^5$ is as $R^4$ defined above or a —$(CH_2)_n$–N($C_1$–$C_6$ alkyl)$_2$ group in which n is 2 or 3;
—$COOR^6$ in which $R^6$ is $C_1$–$C_6$ alkyl unsubstituted or substituted by phenyl or by 1, 2 or 3 hydroxy groups or phenyl;
—$CONHR^7$ in which $R^7$ is hydrogen, phenyl or $C_1$–$C_6$ alkyl substituted by 1, 2 or 3 hydroxy groups or by phenyl;
—$NHSO_2R^8$ in which $R^8$ is $C_1$–$C_6$ alkyl or phenyl unsubstituted or substituted by halogen or by $C_1$–$C_4$ alkyl;

—$N(R^9)_2$, —$NHR^9$ or $OR^9$ wherein $R^9$ is $C_2$–$C_6$ alkyl substituted by 1, 2 or 3 hydroxy groups;
—$NHCOR^{10}$, —$OOCR^{10}$ or —$CH_2OOCR^{10}$ in which $R^{10}$ is $C_1$–$C_6$ alkyl substituted by 1, 2 or 3 hydroxy groups;
—$NHCONH_2$; —NH—$C(NH_2)$=NH; —$C(NH_2)$=NH; —$CH_2NHC(NH_2)$=NH; —$CH_2NH_2$; —$OPO(OH)_2$; —$CH_2OPO(OH)_2$; —$PO(OH)_2$; or a

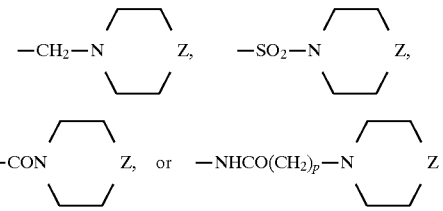

group,
wherein p is 1, 2 or 3 and Z is —$CH_2$—, —O— or N—$R^{11}$ in which $R^{11}$ is hydrogen or is as $R^9$ defined above;
and the pharmaceutically acceptable salts thereof.

2. A compound of formula (I) according to claim 1, wherein:
A and m are defined as above;
$R^1$ is hydrogen or $C_1$–$C_4$ alkyl;
one of $R^2$ and $R^3$ independently is hydrogen and the other is a substituent selected from the group consisting of —$SO_3H$; —$SO_2NH_2$; $COOR^6$ wherein $R^6$ is $C_1$–$C_4$ alkyl or benzyl, —$CONHR^7$ wherein $R^7$ is phenyl or benzyl; —$N(CH_2CH_2OH)_2$; —$NHCH_2CHOHCH_2OH$; —$NHCONH_2$; —$NHC(NH_2)$=NH;

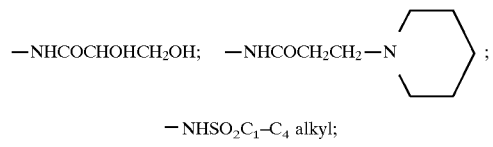

—$OCH_2CHOHCH_2OH$; —$OOCCH_2OH$; —$CH_2NH_2$; —$CH_2OH$; —$C(NH_2)$=NH and —$OPO(OH)_2$; and the pharmaceutically acceptable salts thereof.

3. A compound selected from the group consisting of the Z-diastereomers, the E-diastereomers and mixtures thereof of the formula:
5-sulfo-3-[1,4-dihydroxytetral-2-ylmethylene]-2-oxindole;
5-sulfamoyl-3-[1,4-dihydroxytetral-2-ylmethylene]-2-oxindole;
5-sulfo-3-[-hydroxytetral-2-ylmethylene]-2-oxindole;
5-sulfamoyl-3-[1-hydroxytetral-2-ylmethylene]-2-oxindole;
5-sulfo-3-[3-hydroxytetral-2-ylmethylene]-2-oxindole;
5-sulfamoyl-3-[3-hydroxytetral-2-ylmethylene]-2-oxindole;
5-sulfo-3-[4-hydroxytetral-1-ylmethylene]-2-oxindole;
5-sulfamoyl-3-[4-hydroxytetral-1-ylmethylene]-2-oxindole;
5-carbomethoxy-3-[1,4-dihydroxytetral-2-ylmethylene]-2-oxindole;
5-carbomethoxy-3-[3-hydroxytetral-2-ylmethylene]-2-oxindole;
5-diethanolamino-3-[1,4-dihydroxytetral-2-ylmethylene]-2-oxindole;

5-(2,3-dihydroxypropylamino)-3-(1,4-dihydroxytetral-2-ylmethylene)-2-oxindole;
5-ureido-3-(1,4-dihydroxytetral-2-ylmethylene)-2-oxindole;
5-guanidino-3-(1,4-dihydroxytetral-2-ylmethylene)-2-oxindole;
5-glyceroylamido-3-(1,4-dihydroxytetral-2-ylmethylene)-2-oxindole;
5-(3-piperidinopropionylamino)-3-(1,4-dihydroxytetral-2-ylmethylene)-2-oxindole;
5-mesylamino-3-(1,4-dihydroxytetral-2-ylmethylene)-2-oxindole;
5-glycoloyloxy-3-(1,4-dihydroxytetral-2-ylmethylene)-2-oxindole;
5-(2,3-dihydroxypropoxy)-3-(1,4-dihydroxytetral-2-ylmethylene)-2-oxindole;
5-aminomethyl-3-(1,4-dihydroxytetral-2-ylmethylene)-2-oxindole;
5-amidino-3-(1,4-dihydroxytetral-2-ylmethylene)-2-oxindole;
5-hydroxymethyl-3-(1,4-dihydroxytetral-2-ylmethylene)-2-oxindole;
5-phosphonooxy-3-(1,4-dihydroxytetral-2-ylmethylene)-2-oxindole;
5-sulfo-3-(quinol-4-ylmethylene)-2-oxindole;
5-sulfamoyl-3-(quinol-4-ylmethylene)-2-oxindole;
5-carbomethoxy-3-(quinol-4-ylmethylene)-2-oxindole;
5-diethanolamino-3-(quinol-4-ylmethylene)-2-oxindole;
5-(2,3-dihydroxypropylamino)-3-(quinol-4-ylmethylene)-2-oxindole;
5-ureido-3-(quinol-4-ylmethylene)-2-oxindole;
5-guanidino-3-(quinol-4-ylmethylene)-2-oxindole;
5-glyceroylamido-3-(quinol-4-ylmethylene)-2-oxindole;
5-(3-piperidinopropionylamino)-3-(quinol-4-ylmethylene)-2-oxindole;
5-mesylamino-3-(quinol-4-ylmethylene)-2-oxindole;
5-glycoloyloxy-3-(quinol-4-ylmethylene)-2-oxindole;
5-(2,3-dihydroxypropoxy)-3-(quinol-4-ylmethylene)-2-oxindole;
5-aminomethyl-3-(quinol-4-ylmethylene)-2-oxindole;
5-amidino-3-(quinol-4-ylmethylene)-2-oxindole;
5-hydroxymethyl-3-(quinol-4-ylmethylene)-2-oxindole;
5-phosphonooxy-3-(quinol-4-ylmethylene)-2-oxindole;
5-sulfo-3-(indol-3-ylmethylene)-2-oxindole;
5-sulfamoyl-3-(indol-3-ylmethylene)-2-oxindole;
5-carbomethoxy-3-(indol-3-ylmethylene)-2-oxindole;
5-diethanolamino-3-(indol-3-ylmethylene)-2-oxindole;
5-(2,3-dihydroxypropylamino)-3-(indol-3-ylmethylene)-2-oxindole;
5-ureido-3-(indol-3-ylmethylene)-2-oxindole;
5-guanidino-3-(indol-3-ylmethylene)-2-oxindole;
5-glyceroylamido-3-(indol-3-ylmethylene)-2-oxindole;
5-(3-piperidinopropionylamino)-3-(indol-3-ylethylene)-2-oxindole;
5-mesylamino-3-(indol-3-ylmethylene)-2-oxindole;
5-glycoloyloxy-3-(indol-3-ylmethylene)-2-oxindole;
5-(2,3-dihydroxypropoxy)-3-(indol-3-ylmethylene)-2-oxindole;
5-aminomethyl-3-(indol-3-ylmethylene)-2-oxindole;
5-amidino-3-(indol-3-ylmethylene)-2-oxindole;
5-hydroxymethyl-3-(indol-3-ylmethylene)-2-oxindole;
5-phosphonooxy-3-(indol-3-ylmethylene)-2-oxindole;
3-(5-sulfoindol-3-ylmethylene)-2-oxindole;
3-(5-sulfamoylindol-3-ylmethylene)-2-oxindole;
3-(5-carbomethoxyindol-3-ylmethylene)-2-oxindole;
3-(5-diethanolamino-3-indolylmethylene]-2-oxindole;
3-[5-(2,3-dihydroxypropylamino)-3-indolylmethylene]-2-oxindole;
3-(5-ureido-3-indolylmethylene)-2-oxindole;
3-(5-guanidino-3-indolylmethylene)-2-oxindole;
3-(5-glyceroylamido-3-indolylmethylene)-2-oxindole;
3-[5-(3-piperidinopropionylamino)-3-indolylmethylene]-2-oxindole;
3-(5-mesylamino-3-indolylmethylene)-2-oxindole;
3-(5-glycoloyloxy-3-indolylmethylene)-2-oxindole;
3-[5-(2, 3-dihydroxypropoxy)-3-indolylmethylene]-2-oxindole;
3-(5-aminomethyl-3-indolylmethylene)-2-oxindole;
3-(5-amidino-3-indolylmethylene)-2-oxindole;
3-(5-hydroxymethyl-3-indolylmethylene)-2-oxindole;
3-(5-phosphonooxy-3-indolylmethylene)-2-oxindole;
5-sulfo-3-(naphth-2-ylmethylene)-2-oxindole;
5-sulfamoyl-3-(naphth-2-ylmethylene)-2-oxindole;
5-carbomethoxy-3-(naphth-2-ylmethylene)-2-oxindole;
5-diethanolamino-3-(naphth-2-ylmethylene)-2-oxindole;
5-(2,3-dihydroxypropylamino)-3-(naphth-2-ylmethylene)-2-oxindole;
5-ureido-3-(naphth-2-ylmethylene)-2-oxindole;
5-guanidino-3-(naphth-2-ylmethylene)-2-oxindole;
5-glyceroylamido-3-(naphth-2-ylmethylene)-2-oxindole;
5-(3-piperidinopropionylamino)-3-(naphth-2-ylmethylene)-2-oxindole;
5-mesylamino-3-(naphth-2-ylmethylene)-2-oxindole;
5-glycoloyloxy-3-(naphth-2-ylmethylene)-2-oxindole;
5-(2,3-dihydroxypropoxy)-3-(naphth-2-ylmethylene)-2-oxindole;
5-aminomethyl-3-(naphth-2-ylmethylene)-2-oxindole;
5-amidino-3-(naphth-2-ylmethylene)-2-oxindole;
5-hydroxymethyl-3-(naphth-2-ylmethylene)-2-oxindole;
5-phosphonooxy-3-(naphth-2-ylmethylene)-2-oxindole;
5-sulfo-3-(1-hydroxytetral-2-ylmethylene)-2-oxindole;
5-sulfo-3-(4-hydroxytetral-2-ylmethylene)-2-oxindole;
5-(3-piperidinopropionylamino)-3-(5-methoxyindol-3-ylmethylene)-2-oxindole;
3-[5-(p-chlorophenyl)sulfonylamidoindol-3-ylmethylene]-2-oxindole;
5-carboethoxy-3-(3-hydroxytetral-2-ylmethylene)-2-oxindole;
5-carboethoxy-3-(quinol-4-ylmethylene)-2-oxindole;
5-carboethoxy-3-(5-methoxyindol-3-ylmethylene)-2-oxindole;
3-(5-carboethoxyindol-3-ylmethylene)-2-oxindole;
5-carbobenzyloxy-3-(3-hydroxytetral-2-ylmethylene)-2-oxindole;
5-carbobenzyloxy-3-(quinol-4-ylmethylene)-2-oxindole;
5-carbobenzyloxy-3-(5-methoxyindol-3-ylmethylene)-2-oxindole;

3-(5-carbobenzyloxyindol-3-ylmethylene)-2-oxindole;

5-phenylcarbamoyl-3-(3-hydroxytetral-2-ylmethylene)-2-oxindole;

5-phenylcarbamoyl-3-(quinol-4-ylmethylene)-2-oxindole;

5-phenylcarbamoyl-3-(5-methoxyindol-3-ylmethylene)-2oxindole;

3-(5-phenylcarbamoylindol-3-ylmethylene)-2-oxindole;

5-benzylcarbamoyl-3-(3-hydroxytetral-2-ylmethylene)-2-oxindole;

5-benzylcarbamoyl-3-(quinol-4-ylmethylene)-2-oxindole;

5-benzylcarbamoyl-3-(5-methoxyindol-3-ylmethylene)-2-oxindole;

3-(5-benzylcarbamoylindol-3-ylmethylene)-2-oxindole;

5-carboethoxy-3-(8-hydroxyquinol-5-ylmethylene)-2-oxindole;

5-benzylcarbamoyl-3-(8-hydroxyquinol-5-ylmethylene)-2-oxindole;

5-sulfo-3-(5-methoxyindol-3-ylmethylene)-2-oxindole;

5-(2,3-dihydroxypropylamino)-3-(5-methoxy-3-indolylmethylmethylene)-2-oxindole; or 5-amidino-3-(5-methoxyindol-3-ylmethylene)-2-oxindole; and the pharmaceutically acceptable salts thereof.

4. A pharmaceutical composition, comprising:

an effective amount of the compound of formula (I) of claim 1 or a pharmaceutically acceptable salt thereof combined with a pharmaceutically acceptable carrier and/or diluent.

5. A method of inhibiting tyrosine kinase, comprising:

treating a subject with the compound of claim 1 or a pharmaceutically acceptable salt thereof, to inhibit said tyrosine kinase.

6. A method of inhibiting cell proliferation, comprising:

administering to a subject the compound of claim 1 or a pharmaceutically acceptable salt thereof, as an antiproliferative agent.

7. A method of inhibiting tumor growth, comprising:

administering to a subject the compound of claim 1 or a pharmaceutically acceptable salt thereof, as an antitumor agent.

8. A method of controlling angiogenesis, comprising:

administering to a subject the compound of claim 1 or a pharmaceutically acceptable salt thereof, as an anti-angiogenesis agent.

9. A method of inhibiting, metastasis, comprising:

administering to a subject the compound of claim 1 or a pharmaceutically acceptable salt thereof, as an anti-metastasis agent.

10. A method of treating diabetes, comprising:

administering to a subject the compound of claim 1 or a pharmaceutically acceptable salt thereof, as an antidiabetic agent.

11. A method of treating epidermal hyperproliferation, comprising:

administering to a subject the compound of claim 1 or a pharmaceutically acceptable salt thereof, as an antiepidermal hyperproliferation agent.

12. A method of inhibiting the development of atheromatous plaque and restenosis, comprising:

administering to a subject the compound of claim 1 or a pharmaceutically acceptable salt thereof, as an anti-atheromatous plaque agent or antirestenosis agent.

13. A method of enhancing cancer therapy, comprising:

administering to a subject the compound of claim 1 or a pharmaceutically acceptable salt thereof, as an antitumor agent.

* * * * *